United States Patent [19]

Palanisamy

[11] Patent Number: 4,970,122

[45] Date of Patent: Nov. 13, 1990

[54] MOISTURE SENSOR AND METHOD OF FABRICATION THEREOF

[75] Inventor: Ponnusamy Palanisamy, Kokomo, Ind.

[73] Assignee: Delco Electronics Corporation, Kokomo, Ind.

[21] Appl. No.: 326,128

[22] Filed: Mar. 20, 1989

Related U.S. Application Data

[62] Division of Ser. No. 192,998, May 12, 1988, Pat. No. 4,846,869, which is a division of Ser. No. 087,826, Aug. 21, 1987, Pat. No. 4,797,605.

[51] Int. Cl.[5] .......................... B32B 17/06; B60J 1/02
[52] U.S. Cl. ..................................... 428/432; 428/428; 428/432; 428/913; 296/84.1; 296/97.4
[58] Field of Search ....................... 428/428, 432, 913; 296/84.1, 97.4

[56] References Cited

U.S. PATENT DOCUMENTS

| | | | |
|---|---|---|---|
| 2,877,329 | 3/1959 | Gaiser | 201/73 |
| 3,684,569 | 8/1972 | Milgram | 117/212 |
| 3,864,659 | 2/1975 | Furuuchi | 422/98 |
| 3,989,874 | 11/1976 | Maher | 428/434 |
| 4,109,377 | 8/1978 | Blazick et al. | 29/626 |
| 4,362,656 | 12/1982 | Hormadaly | 428/432 |
| 4,554,493 | 11/1985 | Armstrong | 318/483 |
| 4,655,811 | 4/1987 | Bitter | 65/60.51 |
| 4,665,351 | 5/1987 | Nyberg | 318/483 |
| 4,718,932 | 1/1988 | Pharms | 65/60.2 |

FOREIGN PATENT DOCUMENTS

| | | | |
|---|---|---|---|
| 9032908 | 7/1972 | Japan . | |
| 48007 | 7/1980 | Japan | 324/65 R |

Primary Examiner—Merrell C. Cashion, Jr.
Assistant Examiner—Amy Hulina
Attorney, Agent, or Firm—Robert J. Wallace

[57] ABSTRACT

A moisture sensor consists of an array of spaced apart, highly abrasion-resistant electrodes disposed on the outside surface of the windshield of a vehicle. When moisture is present, the spaces between the electrodes are bridged by the water and the output impedance of the sensor significantly decreases. This signals the presence of moisture. The electrodes have particles of a conductive metal oxide, e.g., ruthenium oxide, dispersed with a glass matrix which is fused to the windshield glass. The electrodes are formulated as an ink including particles of the metal oxide, a glass frit, and an organic binder. The ink is silk screened onto the windshield in the desired electrode pattern. After drying of the ink, the glass frit is fused to the windshield during normal heating of the windshield to shape it in a known windshield shaping (sagging) process. Novel two layer sensor arrangements, providing even greater resistance to abrasion, are also described.

12 Claims, 4 Drawing Sheets

MOISTURE SENSOR AND METHOD OF FABRICATION THEREOF

This is a division of application Ser. No. 192,998 filed on May 12, 1988, now U.S. Pat. No. 4,846,869 which is a division of application Ser. No. 087,826, filed on Aug. 21, 1987 now U.S. Pat. No. 4,797,605.

FIELD OF THE INVENTION

This invention relates to moisture sensors for use with vehicles such as automobiles and the like, and particularly to the electrodes of such sensors.

BACKGROUND OF THE INVENTION

It is known to automatically control the windshield wipers on a vehicle by using a moisture sensor coupled to a wiper system to actuate the system when rain or other water is detected. The sensor is preferably on the windshield surface and wiped during wiper operation. Usually, such sensors are resistive or capacitive and comprise a pattern of spaced apart electrodes on the outside surface of the windshield which provides a normally high or open circuit impedance to a sensor circuit electrically connected to the electrodes. In the presence of moisture from rain or the like, the spaced apart electrodes are bridged by films or drops of water which decreases the impedance across the sensor. This acts as a signal to the sensor circuit which turns on the wiper motors that activate the wiper blades so as to remove moisture from the windshield.

Two classes of materials have heretofore been used to provide the sensor electrodes. One comprises compositions of metal particles and a glass frit which is fused to the windshield. A shortcoming of these compositions is that they lack resistance to abrasion, hence tend to be quickly removed under wiper action.

The other class of materials is that of tin or other metal oxides which are normally sprayed as compounds onto the windshield through an appropriate mask. A shortcoming of these materials is that after they are applied to the windshields, additional processing steps are required to achieve the desired adherence of the material to the windshield and the desired conductive characteristics of the electrodes they form. These additional processing steps are undesirable in that they increase manufacturing costs.

Accordingly, a need exists for improved sensor electrodes which are highly resistive to abrasion and which can be economically applied to windshields.

SUMMARY OF THE INVENTION

The aforesaid need is satisfied by one embodiment of the present invention which is directed to highly abrasion resistant sensor electrodes which comprise films of a composition including glass, for adhering the films to the glass of the windshield, and an electrically conductive metal oxide, e.g., ruthenium oxide, to provide the desired electrical conductance. Preferably, the glass comprises between about 50 to 95 percent (by weight) of the films, such relatively large percentage of glass (in comparison with prior known metal-based films) providing the films with high abrasion resistant characteristics.

The films are formulated as an ink comprising an electrically conductive metal oxide, a glass frit, and an organic vehicle. The ink is applied in the desired electrode pattern, preferably by silk screening, onto the glass windshield, dried, and then heated to fuse the electrode film to the windshield. Preferably, the heating step is performed as part of the normal process of heating the windshield for shaping it. To this end, the film compositions are formulated to cause melting and fusing of the films to the windshield during such windshield shaping process.

Another embodiment of the present invention is directed to a method of fabricating a windshield having electrodes on a surface thereof by depositing a composition comprising an electrically conductive metal oxide on a windshield glass substrate in a preselected pattern to form electrodes. The substrate containing the composition is then placed on a support surface and heated so as to cause it to sag against said surface and for essentially simultaneously fusing the frit of the composition to the substrate so as to bond the electrodes to the substrate.

Novel structural arrangements of the electrode films are provided for further improving the resistance of the films to the abrading action of the wiper blades. In one embodiment of the present invention, the spaces between the electrodes are partially or completely filled with a film of non-conductive glass preferably having a thickness greater than that of the electrode films. This helps ensure the absence of water films bridging the electrodes after the wiper action, thereby preventing excessive wiping action. In still another embodiment of the present invention, a first layer of spaced apart electrodes is completely overlaid with a protective, continuous layer of a more highly resistive material; the combination of the two layers providing a high, but less than open circuit output impedance to the sensor array.

In still a further embodiment of the invention, the material of the inventive films is also used to provide decorative border films used on some windshields. Preferably, both the electrode and border films are applied simultaneously in a single deposition process, thereby further reducing the costs associated with the use of the inventive films.

DESCRIPTION OF THE DRAWINGS

The invention will be better understood from the following detailed description taken with the accompanying drawings in which.

DETAILED DESCRIPTION OF THE INVENTION

Figure 1:
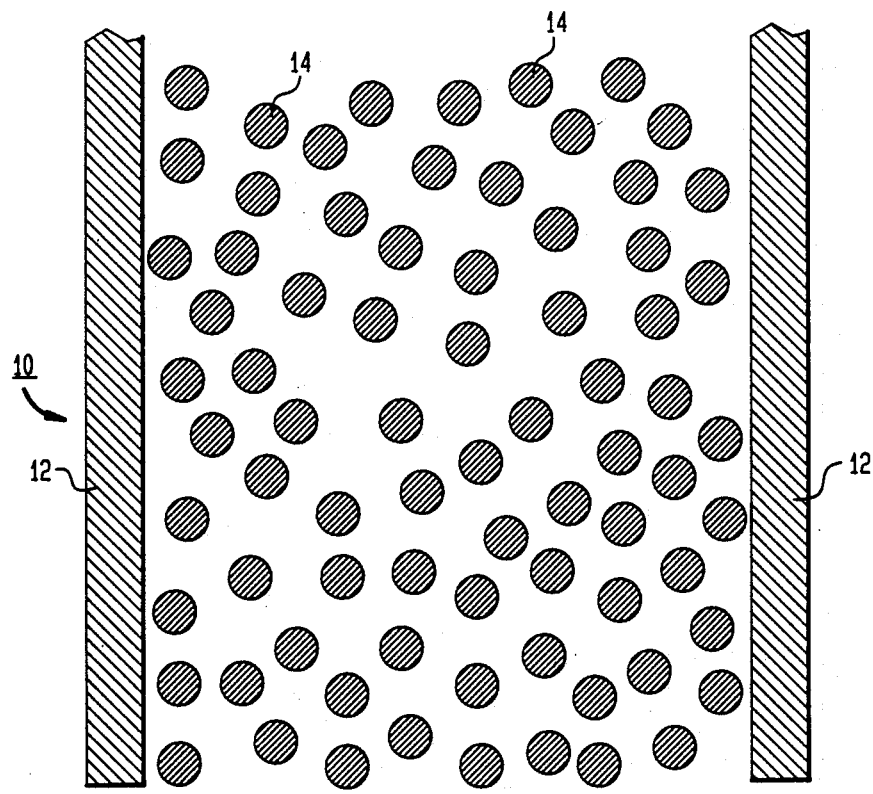
FIG. 1 is a view of an array of electrodes forming a moisture sensor on an automobile windshield.

Moisture sensors for vehicle windshields of the type disclosed in U.S. Pat. No. 4,665,351, issued May 12, 1987, and assigned to General Motors Corporation, are incorporated herein by reference. An example of one such sensor is shown in FIG. 1 herein. The sensor 10, which is disposed on the outside surface of an automobile windshield (also referred to as a substrate), comprises two spaced apart terminal electrodes 12 connected, by known means, to a sensor circuit (not shown) disposed at some location within the vehicle away from the windshield. The space between the two terminal electrodes 12 is almost completely filled with a plurality of small, spaced apart electrodes 14 (shown as circular in this embodiment). In a typical embodiment, the spacings between the different electrodes 14 varies, e.g., from about 10 to 30 mils, and the electrodes have a diameter of around 15 mils. Also, variable diameter electrodes 14 (in a range between around 5 to 50 mils) can be used. As generally known, the varying dimensions of the sensor elements better enable the sensor to detect a range of different moisture conditions varying from fine mist to heavy rain.

Because of the spaces between the electrodes 14, the impedance between the terminals 12 is quite high, being determined principally by the windshield glass between the terminals. However, when moisture is present, the films of water or drops of water bridge the spaces between various ones of the electrodes 14, thereby significantly reducing the electrical impedance therebetween, and eventually complete a relatively low impedance path between the two terminals 12. The reduction of output impedance of the sensor is detected, and the windshield wiper blades are automatically activated.

Because it is generally desired that this automatic control of the wipers be responsive to the moisture conditions on the wiped areas of the windshield, the sensor is also disposed on a wiped area of the windshield. (In the case of sensors comprising non-transparent electrodes, as with the present invention, it is desirable to dispose the sensor out of the usual lines of sight of the driver of the automobile, e.g., on a position of the windshield masked from the driver by the rear-view mirror.) Being thus exposed to the wiping action of the blades, it is necessary that the sensor electrodes be resistant to the abrading action of the wiper blades. This is achieved according to this invention.

In general, the various sensor electrodes, in accordance with this invention, comprise a film (e.g., of a thickness between 2 and 30 microns, and preferably between 5-10 microns) of particles of a conductive metal oxide, e.g., ruthenium oxide, dispersed within a glass binder which is intimately fused to the glass of a windshield (also referred to as a substrate). The composition of the film is selected so that its coefficient of thermal expansion matches (e.g., preferably within 20%) that of the windshield glass. The films have excellent abrasion resistance as measured by standard scribing tests. For example, a diamond stylus is scribed across the films and the depth of the resulting scratches or trenches is measured. In comparison with prior art metal-based films, practically no scratching of the inventive films occurs versus quite deep scratching of the prior art metal-based films. As discussed hereinafter, the greater abrasion resistance provided by the inventive films results from the relatively high percentage of the glass constituent of the films.

Additionally, the inventive films are extremely resistant to various substances likely to be encountered during use of the automobile, e.g., washing solvents, acidic rain, and salt water, and are electrically stable, retaining their electrical resistance values over extended periods of time to within a small percentage of their initial values. Also, there is very good adhesion of the films to the windshield because a glass-to-glass bond is present.

Because the sensor electrodes are patterned, a convenient process for applying the film material to the windshield (preferably while it is in a flat configuration, i.e., before it has been provided with a curved shape) is by known silk screening processes; the film material thus being applied to the glass in the desired final sensor pattern. To this end, the material of the film is formulated as an ink having the necessary (known) characteristics suitable for such silk screen printing. Other known procedures, such as spraying through a mask or transferring a decal, can be used to apply the electrode films to the windshields.

Table 1 lists the materials used to make various ink compositions suitable for silk screening conductive thick films according to this invention. The deposited films, after drying and fusing processes described hereinafter, typically have sheet resistivities in the range between 102 and 106 ohms per square, and typically have coefficients of thermal expansion in a range of 8 to 10 parts per million/°C.

TABLE 1

| Rain Sensor Thick-film Compositions | | |
|---|---|---|
| Major Constituents (By Weight) | Raw Materials Making Up The Constituents | |
| Conducting Oxide (5 to 20%) | $RuO_2$ powder | |
| Glass Frit (40 to 70%) | $Al_2O_3$ 1–5 $B_2O_3$ 5–20 PbO 60–75 $SiO_2$ 5–20 $CO_3O_4$ .1–1 $Mn_2O_3$ .1–1 CuO .2–2 | Percentages by weight of frit |
| Organic vehicle (25 to 40%) | Diethylene glycol monobutyl ether Ethyl cellulose N-200 Igepal CO-430 | |

With reference to Table 1, it is noted that diethylene glycol monobutyl ether is an organic solvent similar to terpeneol. Igepal is the trade name for a wetting agent (an ethoxylated alkyl phenol) made by the GAF Corporation.

While not tested, it is believed that bismuth-ruthenium oxide ($Bi_2Ru_2O_7$) can be used in direct substitution for the ruthenium oxide used in the Table 1 compositions.

Also, different glass frits can be used. For example, frits comprising various percentages of $Al_2O_3$, $B_2O_3$, PbO and $SiO_2$, but containing no $CO_3O_4$, $Mn_2O_3$ and CuO can be used. Techniques for formulating and testing glass frits are well known, see, for example, R W. Vest, "Thick Film Glasses," Final Technical Report for the Period 6/1/77 to 8/31/78, prepared for the Naval Research Laboratory under Contract Number N00173-77-C-0142, Purdue University, Nov. 15, 1978.

The various inks, using the materials in Table 1, are formulated in generally known fashion. For example, the organic vehicle is prepared by combining the ingredients and equilibrating, i.e., dissolving the solid ingredients thereof, at 60° C. for twelve hours. The glass frit is made by heating the frit ingredients at 900° C. for thirty minutes to form a pool of glass and then quenching the glass in cold water to shatter it into particles.

Two different ruthenium oxide powders were used in the various inks. One powder (number one) comprises particles having surface areas of 5 $m^2/g$, particle sizes ranging from 0.5 to 1.5 microns, and average particle sizes of about 1.0 microns. The corresponding characteristics of the particles of the other powder (number 2)

are 20 m²/g, 0.1–1.0 microns, and 0.3 microns, respectively. Powder number one (the smaller surface area particles) results in films having slightly higher resistivity.

The final inks are made by combining all the ingredients and blending them in, e.g., a conventional three roll mill blender.

Table 2 describes examples of individual inks and the characteristics of the resulting films. The films of this table are formulated to be used with conventional and presently commonly used soda-lime-silicate windshield glass having a coefficient of thermal expansion of about 9 parts per million/°C.

(50–95% as earlier indicated), the slope of the curve is not so excessive as to cause manufacturing problems.

Although not shown in Table 2, the coefficient of thermal expansion (between 8 to 10 parts per million/°C., as previously indicated) of each of the sample films listed in Table 2 is sufficiently close to that of the glass of the windshields onto which the films are to be deposited to insure thermal compatibility therebetween. The necessary degree of matching required for the coefficients of thermal expansions of the resulting films and the windshield glass is a function of the thickness of the films; the thicker films requiring a closer matching. If the coefficients of thermal expansion are excessively

TABLE 2

| SAMPLE | $RuO_2$ (WEIGHT % OF INK) | POWDER NUMBER 1 OR 2 (SEE TEXT) | GLASS FRIT WEIGHT % OF INK | WEIGHT % OF FRIT | | | | | | | RESULTING FILM | | |
|---|---|---|---|---|---|---|---|---|---|---|---|---|---|
| | | | | $SiO_2$ | PbO | $B_2O_3$ | $Al_2O_3$ | CuO | $Mn_2O_3$ | $CO_3O_4$ | THICKNESS (MICRON) | SHEET RESISTANCE (ohms/sq.) | GLASS CONTENT (WEIGHT % OF FILM) |
| 1. | 5.0 | 2 | 65.6 | 10 | 79 | 8 | 2 | 0.5 | 0.3 | 0.2 | 7.5 | 360,000 | 92.9 |
| 2. | 7.7 | 2 | 62.1 | 10 | 79 | 8 | 2 | 0.5 | 0.3 | 0.2 | 7.0 | 37,500 | 88.9 |
| 3. | 10.6 | 2 | 58.4 | 10 | 79 | 8 | 2 | 0.5 | 0.3 | 0.2 | 6.3 | 7,500 | 84.6 |
| 4. | 12.4 | 2 | 55.8 | 10 | 79 | 8 | 2 | 0.5 | 0.3 | 0.2 | 6.8 | 1,200 | 81.8 |
| 5. | 15.7 | 2 | 51.8 | 10 | 79 | 8 | 2 | 0.5 | 0.3 | 0.2 | 6.3 | 350 | 76.7 |
| 6. | 5.6 | 1 | 71.4 | 10 | 79 | 8 | 2 | 0.5 | 0.3 | 0.2 | 8.8 | 286,000 | 92.7 |
| 7. | 13.4 | 1 | 59.8 | 10 | 79 | 8 | 2 | 0.5 | 0.3 | 0.2 | 7.8 | 4,300 | 81.7 |
| 8. | 14.6 | 1 | 58.6 | 10 | 79 | 8 | 2 | 0.5 | 0.3 | 0.2 | 7.5 | 1,900 | 80.1 |
| 9. | 15.8 | 1 | 57.9 | 10 | 79 | 8 | 2 | 0.5 | 0.3 | 0.2 | 7.0 | 1,400 | 78.6 |
| 10. | 17.4 | 1 | 55.7 | 10 | 79 | 8 | 2 | 0.5 | 0.3 | 0.2 | 6.3 | 943 | 76.2 |
| 11. | 35.8 | 1 | 35.8 | 10 | 79 | 8 | 2 | 0.5 | 0.3 | 0.2 | 9.5 | 7 | 50.0 |

As shown in Table 2, the percentage of glass in the resulting films ranges between 50 and 92.9%, by weight. Experiments have shown that the abrasion resistance of the films is directly related to the proportion of the glass present; the glass, when fused, being extremely hard and scratch resistant. The proportion of glass used in the inventive films, i.e., preferably not less than about 40%, by weight, is significantly higher than that used in the known metal-based films and is the reason for the greater abrasion resistance of the inventive films.

The relationship between abrasion resistance and the proportion of glass in the films is generally known. The reason larger proportions of glass are not used in the known metal-based films is indicated in FIG. 2.

Figure 2:
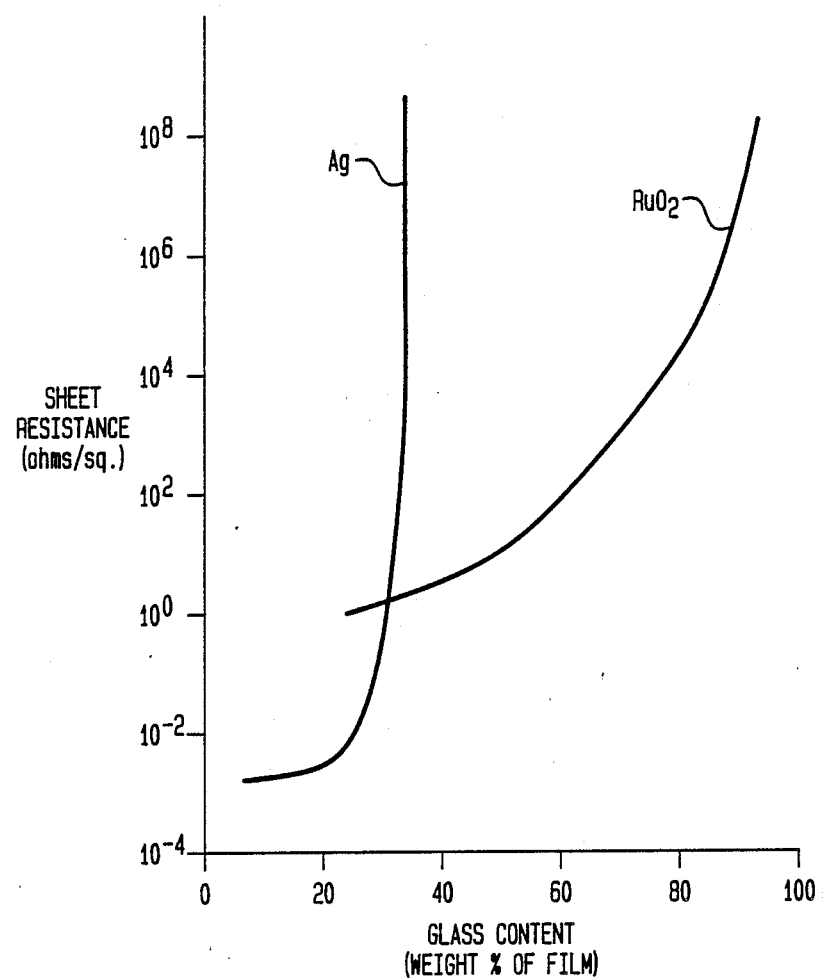
FIG. 2 is a graph plotting glass composition against sheet resistance for different films according to the prior art and according to this invention.

FIG. 2 is a graph plotting glass content (along the X axis, by weight percent) against sheet resistance (along the Y axis, in ohms per square) for a prior known silver-based film (the curve marked Ag) and ruthenium oxide-based films (marked $RuO_2$) according to this invention. Two factors limit the proportion of glass usable in the silver-based films. One is that with percentages of glass reaching about 35%, the sheet resistance of the films becomes excessively high, making the films useless as conductive films. The other factor is that, starting at around a percentage of glass of 25%, the slope of the silver curve becomes quite high, i.e., rapid changes in sheet resistance occur with small changes of glass content. Thus large variations in film resistance can occur within normal manufacturing tolerance variations. This is not generally desirable or acceptable.

In general, other metal-based films are similarly limited with respect to the amount of glass which can be used therewith.

With the inventive films, however, much lower sheet resistances are possible with much larger percentages of glass, and, within the preferred range of percentages mismatched, the resulting films become highly stressed when the windshields are cooled from the "sagging" procedure described hereinafter. Such highly stressed films readily crack and peel from the windshield. Generally, as previously noted, matching within 20% of the temperature coefficients for the thickest films is required.

The resistivity of the electrodes is not critical, and depends upon the particular sensor used. Such sensors are known, hence not described herein.

Having made the desired ink for the particular sensor array being formed, the ink is then preferably silk screened, using known techniques, in the desired pattern (such as, for example, the pattern shown in FIG. 1) onto a windshield substrate. To adhere the films to a windshield (substrate), prior to fusing the films to the windshield, the films are dried at a temperature of about 125° C. for about ten minutes. The organic solvent (diethylene glyco monobutyl ether) is baked out during this drying step.

Thereafter, to fuse and rigidly adhere the deposited film to the glass of the windshield, the entire windshield is heated to an elevated temperature (the organic binder also being removed in the process).

As previously noted, an important feature of the present invention is that the film fusing process is performed as part of the normal processing of the windshield. Thus, additional processing steps, and the costs associated therewith, are avoided.

Figure 3:
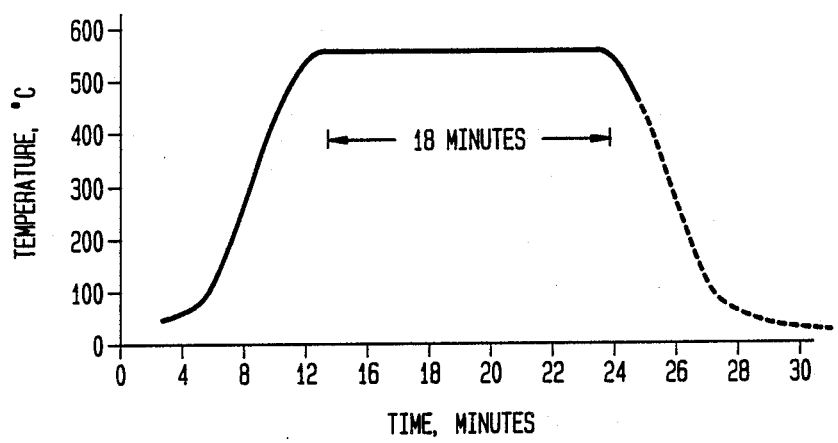
FIGS. 3 and 4 are time-temperature profiles of examples of known processing procedures used in the shaping of automobile windshields, and, in accordance with the invention, for simultaneously fusing sensor electrode films to the windshields.
Figure 4:
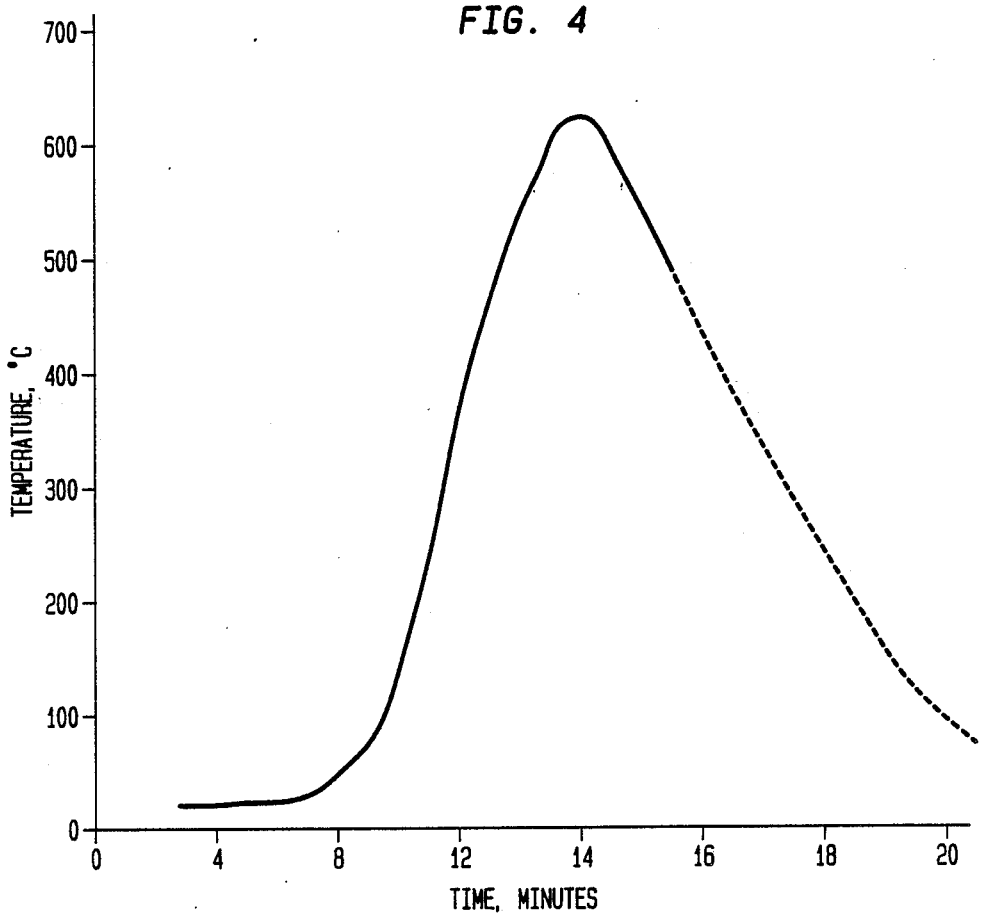

As known, as part of the manufacture of automobile windshields, windshield blanks in planar (flat) configuration are laid horizontally over curved supporting surfaces within an oven and heated to above the softening temperature of the windshield glass. The flat blanks gently sag onto the supporting surfaces, thereby conforming to the shapes thereof. Two examples of the time versus temperature profiles used in such sagging procedures are shown in FIGS. 3 and 4.

The film compositions according to the present invention are formulated such that melting and fusing of the glass frit of the films occurs during the windshield sagging process. While the windshield glass is not heated above its melting temperature, an intimate and strongly adherent bonding of the films to the windshield still results. After cooling, further processing of the windshields can proceed in a normal manner.

The inventive films are not limited in use to windshields having the particular characteristics described herein. Various modifications of the compositions of the films are possible enabling use of the films with windshields having different coefficients of thermal expansion and/or which are processed using different time-temperature sagging profiles. Examples of such modifications, for changing the coefficients of thermal expansion and for changing the temperature at which fusion of the glass of the films occurs, is provided in Table 3 herein below. In general, the desired changes can be achieved solely by changes in the composition of the glass of the films, the particular changes to be made being a function of the particular glass being used. Thus, for each of several classes of glasses, each item including the major constituents thereof shown in the first column of the table, by increasing one of the components listed in the second column and simultaneously decreasing one or more of the components listed in the third column, changes are produced as indicated in the fourth and fifth columns.

although not shown, the layer 18 can completely fill the spaces between the electrodes 14 and even slightly overlap the edges thereof.

Figure 5:
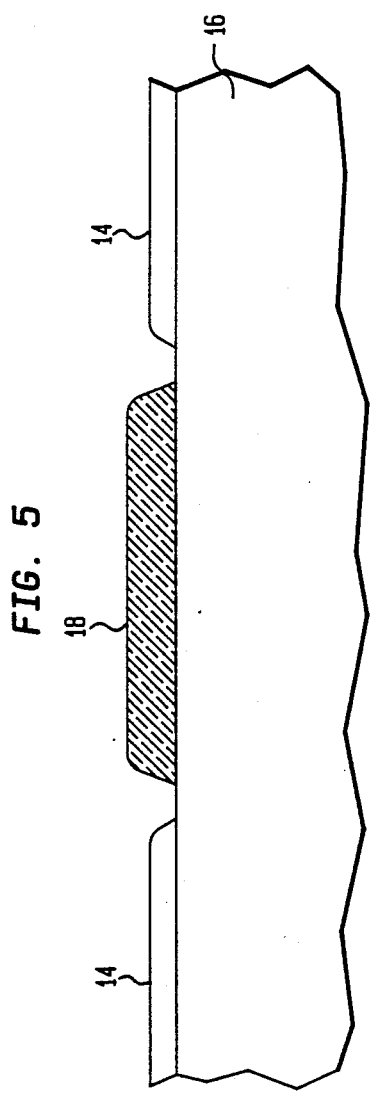
FIGS. 5 and 6 are cross-sectional views of sensor arrangements in accordance with the present invention.

The arrangement shown in FIG. 5 has two advantages:

One is that because the layer 18 is thicker than the electrodes 14, and surrounds them, the wiper blades only engage the layer 18 and not the electrodes. This protects the electrodes against abrasion. Indeed, in this arrangement, the electrodes 14 can even be made of prior known compositions, e.g., the metal-based compositions which are not particularly abrasion resistant. This is possible because of the abrasion protection provided by the layer 18.

The second advantage is that, by at least partially filling the spaces (troughs) between the electrodes 14, a problem caused by the presence of the troughs is avoided. That is, it is found that because of the small lateral dimensions of the troughs, not all the moisture which collects therein can be reached and removed by the wiper blades. Thus, while other wiped areas of the windshield might be moisture free, the moisture remaining in the troughs results in sensor false signals and excessive wiping. This problem is solved by layer 18 in that it is fully wiped by the wipers. This reduces the amount of unwiped moisture. Also, the presence of the layer 18 between the electrodes 14 prevents bridging of the electrodes by moisture remaining in the troughs.

Figure 6:
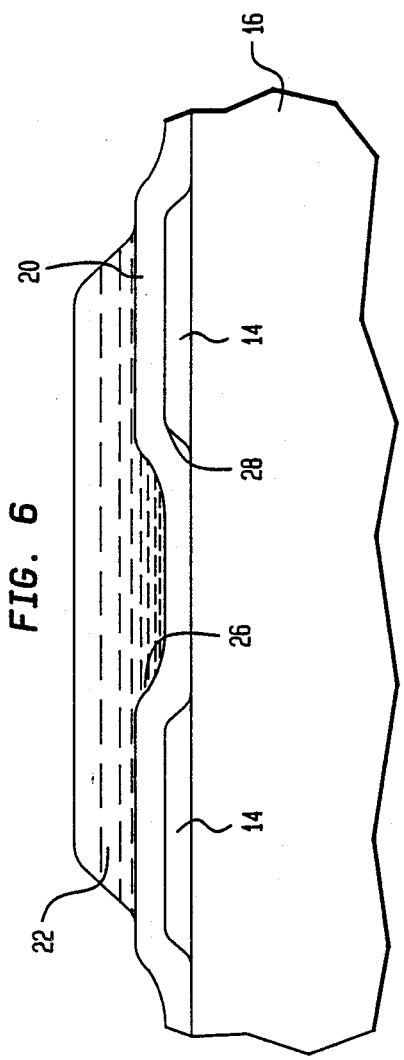

In FIG. 6, a second layer 20 is shown as a continuous, unpatterned film covering both the electrodes 14 and the spaces therebetween. The layer 20 can comprise one

TABLE 3

| Major Components of the glass | Component increased | Component decreased | Effect on Property | |
|---|---|---|---|---|
| | | | Thermal Expansion | Fusing Temp. |
| $PbO$, $B_2O_3$ | $PbO$ | $B_2O_3$ | increases | decreases |
| $PbO$, $SiO_2$ | $PbO$ | $SiO_2$ | increases | decreases |
| $PbO$, $B_2O_3$, $SiO_2$ | $PbO$ | $SiO_2$ | increases | decreases |
| $PbO$, $B_2O_3$, $SiO_2$ | $PbO$ | $B_2O_3$ | increases | decreases |
| $PbO$, $B_2O_3$, $SiO_2$ & $Al_2O_3$ | $Al_2O_3$ | others | decreases | increases |

While, as previously noted, sensor electrodes made of the inventive films can be patterned in known fashion, FIGS. 5 and 6 show two novel sensor electrode arrangements in accordance with the present invention.

In FIG. 5, two sensor electrodes 14 (such as, for example, two adjacent electrodes 14 shown in FIG. 1) are shown on a windshield substrate 16 with a spacing of about 10 mils therebetween. The electrodes 14 have a thickness of about 6 microns (the vertical dimensions in the drawing being greatly exaggerated). Disposed between the electrodes 14 is a layer 18 of a non-conductive material, e.g., glass, having a thickness (e.g., 10 microns) somewhat greater than that of the electrodes 14. The layer 18 can comprise a glass frit similar to the ones used in the compositions listed in Table 2. The layer 18 can be screen printed onto the glass substrate either immediately before or after the screen printing of the electrode array, and the layer 18 can be fused to the windshield during the electrode fusing step. Although not illustrated, various ones of the electrodes 14 are completely surrounded (but not covered) by the layer 18 which, in one embodiment, can be continuous. For example, the layer 18, if used in the FIG. 1 sensor, would substantially completely fill all the open spaces between the electrodes 14. Layer 18 is non-conductive and therefore does not short out the electrodes 14. Also, of the conductive metal oxide compositions disclosed herein, e.g., it can be substantially similar to the composition of the electrodes 14 covered thereby, and can be of equal thickness, but of significantly higher electrical resistivity, e.g. in excess of $10^5$ ohms/square. The presence of the layer 20 reduces the output impedance of the sensor, but the impedance is still sufficiently high as to draw negligible current in dry conditions. When moisture is present (e.g., a water drop 22), the resistance between the electrodes 14 bridged by the drop is significantly decreased. This is because the vertical resistance between electrode 14 and water drop 22 through a vertical portion of layer 20 is relatively low because of the small thickness of the layer 20 and because rain water or water from the road typically has relatively low resistance compared to the lateral resistance of layer 20. Thus, the resistance between two electrodes 14 is significantly reduced when a rain drop 22 overlaps the two electrodes 14.

In the fabrication of the arrangement shown in FIG. 6, the electrodes 14 are first deposited and dried, the layer 20 is thereafter deposited and dried, and both layers are simultaneously fused to each other and to the windshield glass in a subsequent windshield sagging process. An inherent result of the two successive deposition steps is that the edges 26 of the troughs in the layer 20 between the electrodes 14 are substantially more rounded than the edges 28 of the electrodes 14. These rounded edges 26 both reduce the abrasive action of the wiper blades against the layer 20 and facilitate entry of the blades into the troughs for more effective moisture removal. Also, because of the protection provided by the covering layer 20, the covered electrodes 14 can be of other materials, such as the prior known metal based films, which are not abrasion resistant.

As mentioned, a principal advantage of the invention is that the fusing of the films to the windshields can be accomplished during the normal windshield sagging process, thereby reducing the costs associated with applying the inventive films. Still further costs can be eliminated by modifying certain standard windshield processing steps.

For example, it is common to apply, by silk screening, or spaying or the like, a decorative (shadow) border on the windshield prior to the windshield sagging process. However, in accordance with this invention, the border material can be replaced with the identical inventive materials described herein for use as sensor films. Thus, by simultaneously applying the same material to serve both as the decorative border and as the sensor films, the otherwise additional costs for applying the sensor films are substantially completely eliminated.

The embodiments of the invention in which an exclusive property or privilege is claimed are defined as follows:

1. A glass windshield having a conductive pattern of electrodes on a surface thereof, said electrodes comprising a powder of ruthenium oxide embedded within a glass matrix fused to the glass of said windshield, wherein said electrodes are made from an ink comprising 5-20 weight % ruthenium oxide, 40-70 weight % glass frit, and 25-40 weight % organic vehicle which is silk screened onto the glass windshield, dried to remove the organic vehicle and fused to the glass of said windshield, said electrodes having a coefficient of thermal expansion within 20% of that of the glass of said windshield and wherein the glass of said matrix has a melting temperature below the softening temperature of the glass of said windshield.

2. The windshield of claim 1 in which the glass of said electrodes comprises at least 40% thereof, by weight.

3. The windshield of claim 1 wherein the spaces between electrodes are filled with a film of non-conductive glass.

4. The windshield of claim 1 wherein the spaces between electrodes are filled with a film of non-conductive glass that preferably has a thickness greater than the thickness of said electrodes.

5. The glass windshield of claim 1 wherein said electrodes have a film covering them that is more abrasion-resistant than said electrodes and that has a glass matrix in which the glass has a fusion temperature below the softening temperature of the glass of the windshield.

6. The glass windshield of claim 1 wherein said electrodes have a film covering them that is about of the same thickness as said electrodes but that has a significantly higher electrical resistance than said electrodes.

7. A glass windshield having a conductive pattern of electrodes on a surface thereof, said electrodes comprising a powder of a conductive metal oxide embedded within a glass matrix fused to the glass of said windshield wherein said electrodes are made from an ink comprising 5-20 weight % conductive metal oxide, 40-70 weight % glass frit and 25-40 weight % organic vehicle which is silk screened onto the glass windshield, dried to remove the organic vehicle and fused to the glass of said windshield, said electrodes having a thickness between 2 and 30 microns, a resistivity between 102 and 105 ohms/square, and a coefficient of thermal expansion within 20% of that of the glass of said windshield, the glass of said electrodes comprising at least 40% or greater thereof, by weight and, wherein said electrodes are made from an ink comprising 5-20 weight % ruthenium oxide, 40-70 weight % glass frit, and 25-40 weight % organic vehicle which is silk screened onto the glass windshield, dried to remove the organic vehicle and fused to the glass of said windshield, said electrodes having a coefficient of thermal expansion within 20% of that of the glass of said windshield and wherein the glass of said matrix has a melting temperature below the softening temperature of the glass of said windshield.

8. The windshield of claim 7 wherein spaces between electrodes are filled with a film of non-conductive glass.

9. The windshield of claim 7 wherein the spaces between electrodes are filled with a film of non-conductive glass that preferably has a thickness greater than the thickness of said electrodes.

10. The glass windshield of claim 7 wherein said electrodes have a film covering them that is more abrasion-resistant than said electrodes and that has a glass matrix in which the glass has a fusion temperature below the softening temperature of the glass of the windshield.

11. The glass windshield of claim 7 wherein said electrodes have a film covering them that is about of the same thickness as said electrodes but that has a significantly higher electrical resistance than said electrodes.

12. The glass windshield of claim 7 wherein said electrodes have a film covering them in which the film is more abrasion-resistant than said electrodes, has an electrical resistance that is significantly higher than the electrical resistance of said electrodes, and the film is of a thickness not significantly greater than that of said electrodes, with said covering film comprising a glass matrix in which the glass of the matrix has a fusion temperature below the softening temperature of the glass of the windshield.

* * * * *